United States Patent [19]
Blomer et al.

[11] 4,060,075
[45] Nov. 29, 1977

[54] SPLINT AND BODY-SUPPORT DEVICE

[76] Inventors: Alois Blomer, Gildenstrasse 61, 4390 Gladbeck; Hans Schulze, Fliederweg 8, 5931 Netphen-Deuz, both of Germany

[21] Appl. No.: 646,978

[22] Filed: Jan. 6, 1976

[51] Int. Cl.² .............................................. A61F 5/04
[52] U.S. Cl. .................................................... 128/90
[58] Field of Search ..................... 128/90, 89, 87, 165, 128/166

[56] References Cited
U.S. PATENT DOCUMENTS

| | | | |
|---|---|---|---|
| 3,373,741 | 3/1968 | Hill et al. | 128/90 |
| 3,375,822 | 4/1968 | Rose | 128/90 |
| 3,415,243 | 12/1968 | Sheldon | 128/90 |
| 3,618,599 | 11/1971 | Beightol | 128/90 |
| 3,674,021 | 7/1972 | Snyder et al. | 128/90 |
| 3,905,376 | 9/1975 | Johnson et al. | 128/90 X |
| 3,930,496 | 1/1976 | Gibbons | 128/90 |

Primary Examiner—John D. Yasko
Attorney, Agent, or Firm—Karl F. Ross

[57] ABSTRACT

A splint or other body-support device adapted to fit around or along a body portion of a human or animal subject is formed with a closed compartment containing capsules or the like of two mutually reactive substances capable of hardening or foaming in situ to form a hardenable mass stabilizing the shape of the device. The device may comprise an envelope of a flexible material which may be kneaded or deformed to rupture the capsules and mix the reactive substances.

15 Claims, 5 Drawing Figures

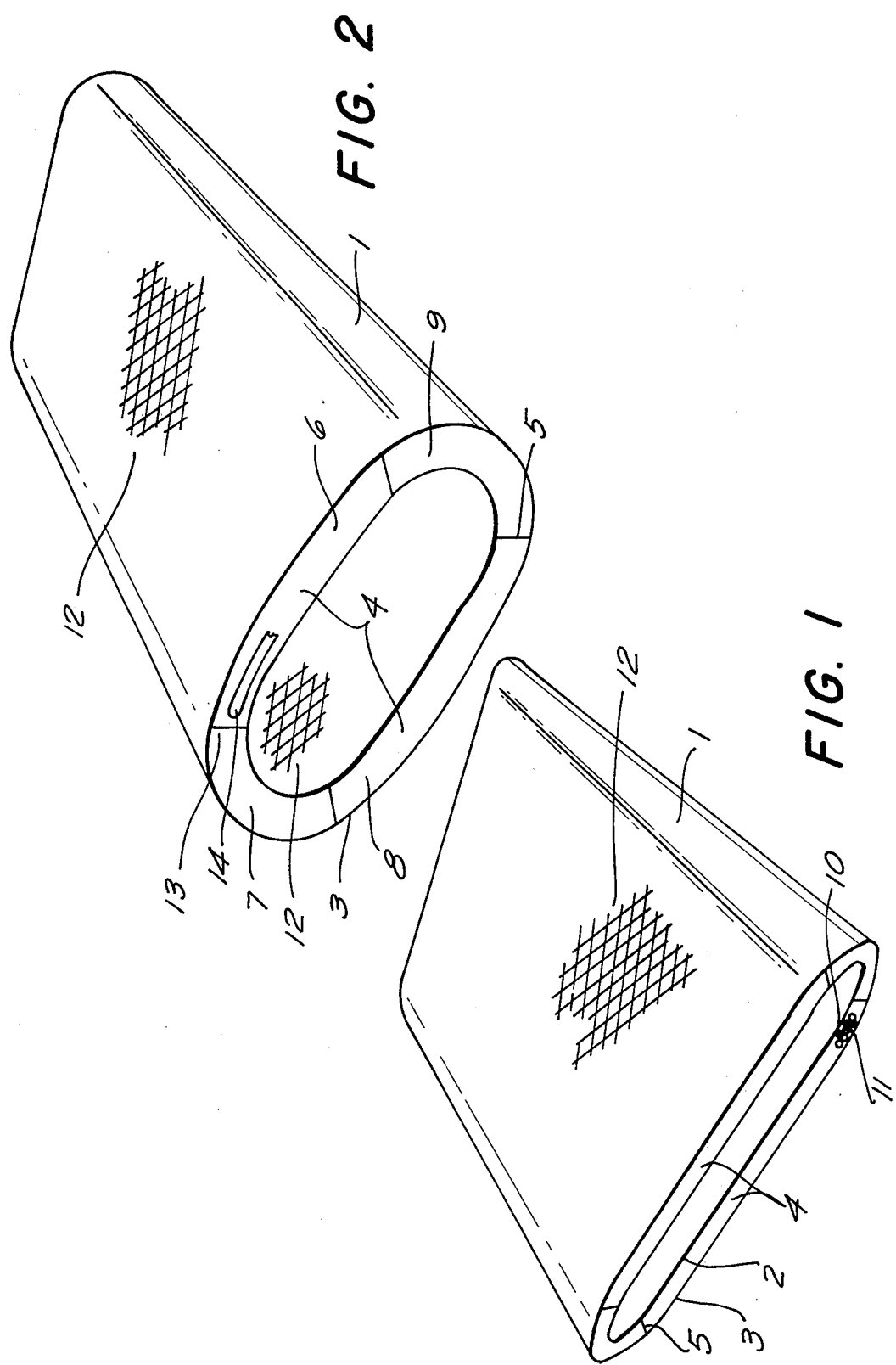

SPLINT AND BODY-SUPPORT DEVICE

FIELD OF THE INVENTION

The present invention relates to a device for supporting a portion of a human or animal body, e.g. a brace or splint, which can be readily conformed to the body portion and, more particularly, to a supporting or splinting device for supporting a portion of a human or animal body.

BACKGROUND OF THE INVENTION

Both in human therapy and in veterinary medicine it is frequently required to provide support for a body portion of the subject or patient, either for immobilizing parts of the supported portion, immobilizing the supported portion relative to other parts of the body or to provide load-bearing members adapted to take up forces which should not be applied to the supported body portion.

Typical of such supporting devices are braces and splints. However, for the present purposes it should be noted that the term "body support" or "splint" may be used interchangeably to refer to any device which can be shaped to the contours of a human or animal body or a portion thereof to stabilize such portion, to provide a load-supporting structure and encase the same fully or partially, or a structure cushioning the portions of the body against impact or other detrimental environmental effects.

Thus the terms will include braces, splints, stiffening members and cushioning structures to support broken limbs, to provide therapeutic regulation of the stance of the body, to impart a desired position to a supported portion or to immobilize the supported portion relative to other parts of the body.

Various devices for the latter purposes have been proposed heretofore and one can generally recognize such qualities in plaster casts, splints and braces of wood, synthetic resin, plastic or metal.

Generally the conventional devices are designed to limit the movement of a part of the body, e.g., the arm, leg, foot or neck, to allow healing of muscular disorders, joint disorders or fractures, to provide structural support for the body portions so that the patient or subject can have improved mobility or to prevent movement of body portions where such movement would be detrimental to healing of burns or the like. For example, there are disorders such as irritations in which absolute or partial immobility of a body member is required for healing.

The procedure in the past has been to place the body portion or member in the desired position at which healing will be optimum and to apply a plaster strip (after wetting) so that, upon hardening of the resulting cast, a change from this position will be resisted.

While the body portion or member is held generally in a desired position, there nevertheless is the requirement that some mobility be provided. Such mobility is necessary to prevent atrophying, or blood-circulation disorders, or to prevent deterioration of the skin resulting from lack of activity. Furthermore, total immobility may affect other portions of the body and may even adversely affect the functioning of the immobilized part or member if the immobilization is to extend over prolonged periods.

Disorders which must be treated by casts, splints, braces and other immobilizing (generally: supporting) devices occur daily in sports, hazardous occupations and even day-to-day life, with humans as well as with animals.

It has been found that similar problems arise in orthopedics with disorders of the bone structure and musculature systems, e.g., curvature of the legs, foot disorders, disorders of the spinal column and deterioration of the joints as a result of congenital defects, diseases and age. In these cases as well it is necessary to immobilize or support portions of the body and supporting devices in the form of corsets, cases and prostheses or the like are required and may be formed from plaster or, expecially in the form of prostheses-carrying cases from stiff but cushioning synthetic materials. In all circumstances, however, these devices must be conformed to the body.

In general there are three methods used in the art for providing supporting devices for the purposes described.

Probably the best known and most widely used technique is the application of a plaster cast using plaster-containing bands or strips which are immersed in water and wound upon the body portions to be supported. By hand-shaping the plaster mass can be so molded that the cast can conform to the body portions and also assume substantially any position in which it may be desirable to support the body. By chemical reaction or evaporation of water the support hardens and maintains its preset position and shape.

Another type of support is provided by use of air-impermeable bags which are filled with a granular material and are laid upon the portion of the body to be supported. These bags are evacuated by a pump so that atmospheric pressure applies to the bag a force which presses against the filling and makes the bag relatively stiff and immovable. It is also known to connect the interior of such bags with an air source so that the bag can be firmly mounted upon the body portion to be supported.

A third type of supporting device utilizes a synthetic-resin in liquid or plastic form, with or without reinforcing inlays of a textile fabric, which are applied to the body portion to be supported and are hardened by heat or ultraviolet radiation.

The disadvantages of the different techniques are set forth in the following Table:

|  | Plaster of Paris/ Starch-Bandage | Vacuum bag | Synthetic-Resin Bandage |
|---|---|---|---|
| Time | Long time needed for hardening, a number of hours up to days. | Short time for achieving hardness, not formable due to lack of plasticity. | Medium time for hardening, little formability. |
| Weight | High because of density of material, the necessary volume and inserts. | Medium high, dependent on filling material in bags, but constant pressure on the part of the body | Low because of small density and little needed volume, |

|  | | | -continued | |
| --- | --- | --- | --- | --- |
| | | | and danger of circulatory disorders, so that model is only a temporary arrangement, e.g. for transport purposes, but unusable for therapeutic treatment. | |
| Porosity | Little receptivity for steam, i.e. water, Plaster of Paris is hygroscopic. Through water intake diminishes considerably. Disruptive absorption when illuminated by X-Ray. | | Nonporous for air and water, i.e. steam. Short usable service life. Little for transparency X-rays. | Little porosity because of supports for air and water. Good transparency for X-rays. |
| Sensitivity | Not waterproof. Unbreakable only after increased strength; i.e. weight. | | Sensitive to mechanical damage of bag, limitedly stable. | Generally waterproof and mechanically stable. |
| Equipment | Little, manual skill is necessary | | Considerable, since special bag forms are needed for each part of the body and a vacuum pump | Medium, since mixing apparatus and gear are necessary for introducing hardness |

From the Table it will be apparent that none of the conventional techniques is fully satisfactory. In the past the short period required to apply the support has given a slight advantage to the plaster cast or strip, although such supports have disadvantages when the body portion must be subjected to X-ray. Recently synthetic-resin supports have become a more interesting alternative because of X-ray transparency. However, their relatively high cost has prevented them from fully replacing the plaster cast. In general the least satisfactory of the three techniques has been the use of the evacuated bag.

OBJECTS OF THE INVENTION

It is the principal object of the present invention to provide an improved device for the immobilization and/or support of body portions of human and animal subjects which is free from the disadvantages of of earlier systems as enumerated above, has widespread application to patient requirements of all types and satisfactorily provides substantially all of the requirements for an immobilization or support structure.

Still another object of the invention is to provide a readily applicable immobilization or support device for body portions of humans and animals which is of relatively low cost.

SUMMARY OF THE INVENTION

We have found that these objects can be achieved in a device for the immobilization and/or support of body portions of human and animal subjects, which avoids the aforementioned drawbacks and provides for conformity of the device to any body portion in any position for every type of patient.

According to the invention, the device is provided with an envelope of a flexible material having at least one partially closed compartment containing in separate regions thereof at least two reaction components capable of interaction but separated from one another prior to use of the device.

The device is constructed to permit the reaction components to be mixed together and undergo a reaction which produces a substance capable of hardening and thereby stiffening the device in the position in which it has been placed about the body portion of the patient.

Generally means is provided to maintain the components separated from one another within the compartment, such means being directly or indirectly destructible to allow the components to be mixed together. Such means may include membranes, coatings, skins, partitions or other structures which are capable of destruction by pressure, tension, attrition or aging, ultrasonic vibration, electromagnetic, thermal or other radiation, temperature or the like. The term "destructible" is here used in its broadest sense to mean breakdown of continuity, either by penetration (rupture), actual chemical decomposition, or change in physical state as in the case of evaporation or solubilization.

We have found that such means allows precise adjustment of the reaction time for the two components which reaction time preferably is from 5 to 30 minutes, i.e., the hardening takes place to the point that at least initial stabilization of the structure can be detected.

Control of the reaction time utilizes the fact that the thermally destructible means can, for example, have selected techniques so that greater activation, e.g., by kneading or compression of the device, is required to obtain mixing.

During this reaction time, therefore, the device and, consequently, the reaction mixture is fully plastically deformable so that it can be applied to the body portion to be immobilized and/or supported in a simple and rapid manner. Full conformity to the shape of the body portion is also possible by reason of the plastic character of the device including the reaction mixture.

The device according to the invention requires, prior to the application, only such handling as will destroy the separating means between the components in the compartment of the device to enable these components to interreact, whereup the device can be applied in the form of strips or in another suitable configuration.

The device according to the invention is extremely light so that unnecessary loading of the patient is avoided. Furthermore, in the event the envelope is formed from a gas-permeable material, the reaction mixture can, upon hardening, be an open-cell structure of gas permeable foamed synthetic-resin so that the entire device is permeable to air and water vapor. In addition, by proper choice of the foamable reaction mixture, the system may be made either water impermeable or sufficiently porous as to allow the passage of liquid water. This prevents deterioration of the skin in regions enclosed by or in contact with the device, prevents damp spots from forming between the skin and the device, and makes the wearing of the device more comfortable.

The system of the present invention has been found to be practically insensitive to water and soaps, i.e., soapy water, so that washing and bathing of the patient wearing the device can proceed unimpaired. In addition, submerged massages and the like can also be undertaken while the patient is wearing the device.

Furthermore, the device has a high degree of resilience so that it can be taken off, cleaned and reapplied if desired. The mechanical stability of the device is so great that many manipulations may be undertaken by the patient or various treatments may be applied to the patient without fear to the supported or immobilized part. Finally, the device, formed by enclosing in a compartment containing the reaction components in a flexible material, has rounded surfaces free from sharp edges or other contours which themselves may be detrimental and has a body-compatible configuration with a certain amount of yieldability so that the device does not press internally into other parts of the body.

It has been found that the device can be fabricated at particularly low cost and can be applied with the same advantage. Such systems are not required for the preparation of the device prior to application and a most important advantage has been found in the ability to apply the device while monitoring the position of the body part by fluoroscopy or another X-ray monitoring system.

According to a feature of the invention, the reaction components are mixed together and caused to react not only by mechanically applied pressure from the exterior but even by an internally generated gas pressure. Thus, if the reaction components are separated by coatings or membranes and include low-boiling point components which are capable of evaporation at body temperature, the device may be applied to the body part, whereupon the patient's body temperature can cause evaporation of the low boiling point substances, breakdown of the membranes and interaction of the components.

Still another important advantage of the system according to the invention resides in the totally new approach to application of the device to the patient. This technique is comparatively less expensive than earlier methods.

For example, the earlier approaches to the formation of supporting corsets or belts, it was necessary to provide negative and positive molds or dies conforming to the body of the patient. This was time consuming and required numerous fittings and adjustments. The system of the present invention permits application to the body directly and conforming of the device as desired. For example, it permits conforming the device to the body while the body is subjected to a therapeutic treatment such as muscular distortion or change.

When the device is used as an upper arm splint or support, where immobilization of the body portion is required as part of a therepeutic treatment, the rapid setting time permits the treatment to be combined with immediate application of the immobilizing device in a period of several minutes, without difficulty.

According to the invention, the envelope may be a tube or the like closed at its ends and formed internally with at least one compartment but, if desired, with two or more longitudinal compartments. It is also possible to form the envelope from a foil strip which can be provided with channels, recesses, depressions or concavities containing the reaction component and closed by a cover layer.

The components may be introduced into a common component as microcapsules, each having a destructible coating, or the compartment may be subdivided by partitions of paraffin into larger spaces containing the reaction components so that the latter are effectively macrocapsules.

The compartments may be formed from the components themselves, in which case the mass of each compartment may have a reactive core constituting most of the material of the compartment and covered by a thin solid shell of the same material as a so-called "self-capsule".

The compartment may contain a bag or the like separating one compartment from the other and destructible by tearing upon the application of tension.

According to still another feature of the invention the compartment containing the reactive component may be provided with substances imparting a desired coloration to the finished structure or some other optical characteristic. The coloring matter may also serve to permit determination of the degree of hardening can be determined.

By varying the quantities of the individual components it is possible to determine the parameter of the resulting reaction. For example, the hardness, porosity, resilience and ultimate volume of the hardened product can be determined by the proportions of the reactive components. Residues of the two components are included within the reactive mass and envelope without causing difficulties.

According to a further feature of the invention, the space containing the respective reaction components, whether as tubes, recesses, microcapsules, macrocapsules, self-capsules, bags, sleeves or the like, are disposed in such number and spatial relationship as to obtain the desired progress of the reaction. There are several modes of operation which can be used in this respect and it should be noted that in all cases it is important to limit the reaction temperature to a maximum of about 50° C to prevent injury to the patient and to control the hardening time to insure that sufficient time is available to apply the device to the body portion of the patient. In general, the reaction will be exothermic and hence the components should be provided in such quantity, spacing and physical arrangement as to prevent any portions of the device from exceeding the indicated temperature.

After hardening, for which a period of about 5 to 30 minutes is preferred, the device is fully loadable, i.e., can receive the maximum stress to which it will be subjected. The pressure upon the body portion is negligible or nonexistent except for the minimum pressure which is required to stabilize or immobilize the body portion. It has been found that the device can be worn for an unlimited duration since there is no blockage of blood circulation. Furthermore, the gradual hardening of the reaction product can be effected within limits required by the medical necessities.

We have found that a particularly advantageous mode of realization of the invention provides the device for immobilizing and/or supporting body portions of human or animal subjects from a tube subdivided internally into a plurality of chambers together forming the aforementioned component in which the reaction is effected. Consequently, the interior space of the tube forms the reaction component.

While we prefer to provide the two reactive components in each chamber of the compartment or in separate chambers of the compartment so that mixing will form the reaction mixture in at least some of the chambers of the compartment, it is also possible to introduce the previously formed mixture of the reaction components into the chamber or compartment forming the interior of the tube before the device is applied to the body portions of the subject. This arrangement has been found especially effective for dorsal or volar splints of optional length.

According to another feature of the invention, the device for immobilizing or supporting body parts of human and animal subjects, developed in accordance with the principle of the present invention, comprises a double-wall tube of elastic material, between the walls of which one or more compartments for the reaction mixture can be provided. Preferably the compartment is subdivided into the aforementioned chambers by partitions or ribs having openings permitting communication between the chambers of the compartment. In this manner at least two cells are formed in the double wall of the tube surrounding the free open cross section of the interior of the tube. The elasticity of the inner tube wall is so selected that it can automatically assume the shape of the body portion to be immobilized or supported. In other words the inner tube wall has the characteristics of an elastic stocking which can be drawn onto an appendage of the body and conform itself to the shape thereof.

The elasticity of the outer tube wall is so selected that it can accommodate the appendage and plastic reaction mixture until it hardens into the form of the appendage to which the device is applied.

The device can for example be made from a cotton stocking fabric which can simply be drawn over the body portion to be supported or immobilized. Even in this embodiment it is desirable to provide cells in the space between the walls and to provide the components in these cells for reaction upon application of pressure, e.g., by kneading, before or after the tube is drawn over the appendage. Of course it is possible here to introduce the preformed reaction mixture into the cells or some of them after the sleeve has been applied to the subject.

Because of the elasticity and flexibility of the inner and outer tube walls, the device fully automatically conforms itself to the shape of the appendage to which it is applied and applies uniform pressure to this body portion.

The tube walls can be made from fabric of materials which are elastic in both the longitudinal and transverse directions for both the outer and inner sleeve walls, preferably as noted from cotton stocking.

The reactive compartments preferably form, upon reaction, a foamable synthetic resin, e.g., because of intrinsic foaming agents or moisture available in the stocking material. As a result, the hardened body of the synthetic-resin filler can comprise a core of relatively high-density low-foaming material and inner and outer sheaths of relatively low-density, highly foamed material. These foamed sheaths provide a highly desirable cushioning effect. When the reaction components are di- or polyisocyanates and dipolyols as can be used for the production of polyurethane resins, the reaction does not give rise to any by-products or decomposition products which are released and so there is no skin irritation or adverse effect upon the respiratory system. Removal of the splint can be effected with an oscillatory saw without any difficulties arising from dust formation.

Advantageously, the ribs or webs which divide the interior of the wall space into cells have a porosity or permeability to the reaction component and/or the reaction mixture so that the reaction mixture, upon solidification, surrounds these ribs on all sides and the latter are embedded in the solidifying resin as stiffening webs. The ribs can themselves be made of elastic material.

It has been found to be advantageous, according to another embodiment of the invention, to provide a plurality of longitudinally extending cells within the tube but to fill less than all of them with the reaction mixture. Thus, when two cells are provided, we may fill only one of them with the reaction mixture. In this case, one cell is separated from the other by impermeable partitions, ribs or the like. The reaction components may both be included in the one cell to contain the reaction mixture while the other cell is empty. Upon hardening, there will be no stiffening in the region of the second cell although the wall of the tube in this region will seize the body part with its intrinsic elasticity. The hardened synthetic-resin material will thus lie on only one side of the appendage to be protected, immobilized or supported. This structure has been found to be particularly desirable as a splint.

The walls of the device can, according to another feature of the invention, be provided with joints and/or connecting elements so that the device can be removed and reapplied easily and repeatedly. While this has been found to be desirable in orthopedics, it has also been found to be important for surgery. The joints or coupling elements can be slide fasteners or toggle joints. These elements can be previously formed in the walls of the device, e.g., by being stitched to the tubing fabric before the reaction and application, or can be applied to the hardened structure after separation, e.g., with a saw. Of course joints can also be made from bands or by section-wise sawing off of the tube or by partitions between cells which are not permeated by the reaction product.

BRIEF DESCRIPTION OF THE DRAWING

The above and other objects, features and advantages of the present invention will become more readily apparent from the following description, reference being made to the accompanying drawing in which:

FIG. 1 is a perspective view of the device according to the invention in the form of a double wall hose or sleeve for splinting a body appendage such as an arm or leg;

FIG. 2 shows the device after reaction of the components;

SPECIFIC DESCRIPTION

Figure 4:
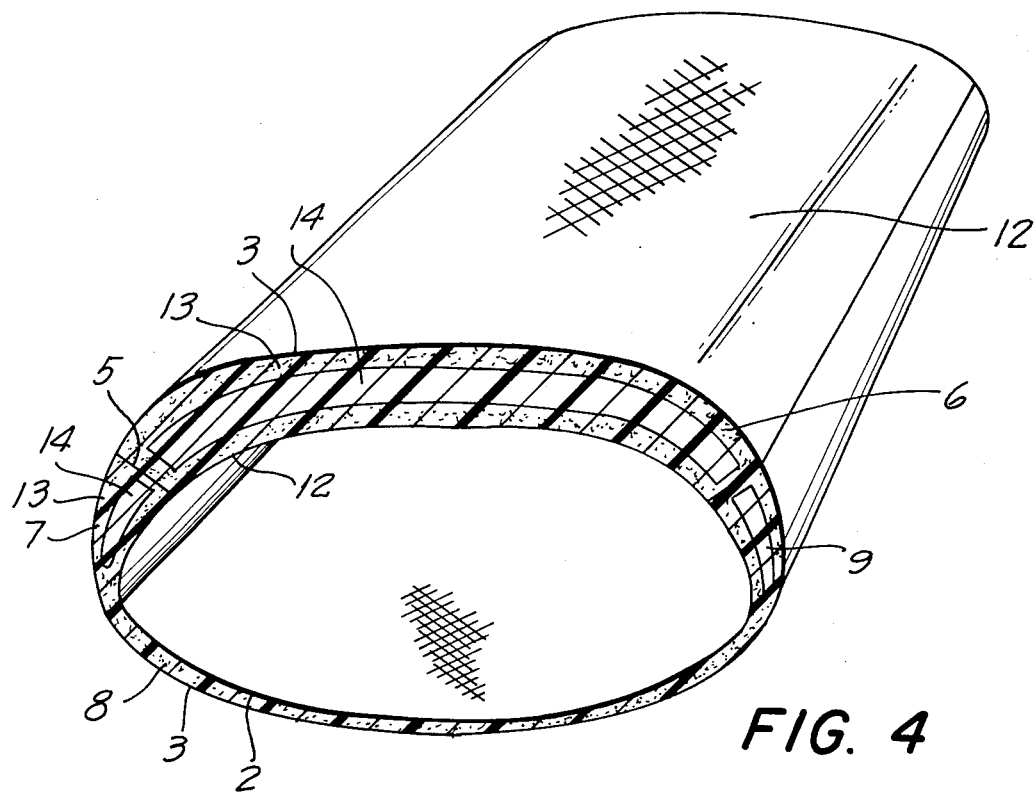
FIG. 4 is a diagrammatical view of the device used as a splint.

FIGS. 1 and 2 show the device according to the invention in the form of a double hose or sleeve (tube) arrangement which can be applied over a body appendage such as a limb to form a splint or immobilizing structure. The double sleeve 1 has an inner wall 2 and an outer wall 3 defining between them a compartment 4 which is subdivided by the webs 5 into cells 6, 7, 8, 9.

The cells 6 – 9 receive the spaces 10, 11 containing respective components of the reaction mixture. In this case, the component spaces are in the form of individual capsules as best shown in FIG. 1. Thus the components are held apart in the collapsed state of the tube.

The inner and outer walls 2 and 3 are formed from elastic fabric which is shown only symbolically in the drawing at 12. The coatings of the capsules are broken and the reaction mixture is formed by applying external pressure to the tubing. In its simplest form this pressure may be applied by a pressure roller drawn over the tubing and pressing it firmly against a hard surface. The rolling operation mixes the two reaction components which begin to foam as is common with polyurethane resins in contact with the moisture-containing fabric.

During the reaction, the tubing 1 is drawn over the body appendage to be supported or immobilized and, because of the elasticity of the inner wall 2, analogous to that of a support stocking or elastic bandage, conform to the contours of this appendage which is temporarily positioned in the form in which the appendage is to be held. The outer wall 3 likewise conforms to the contour of the appendage except that it is expanded outwardly by the hardening synthetic resin. In other words, conformity of the device to the body portion is automatic so that special care need not be taken by the physician to ensure such conformity.

The webs 5 are spaced apart longitudinally of the tubing or are provided with holes so that they are permeable to the reaction mixture, the reaction mixture passing through these ribs 5 and filling all of the cells 6 – 9 while embedding the ribs 5. The latter thus function after hardening as stiffening ribs.

Figure 3:
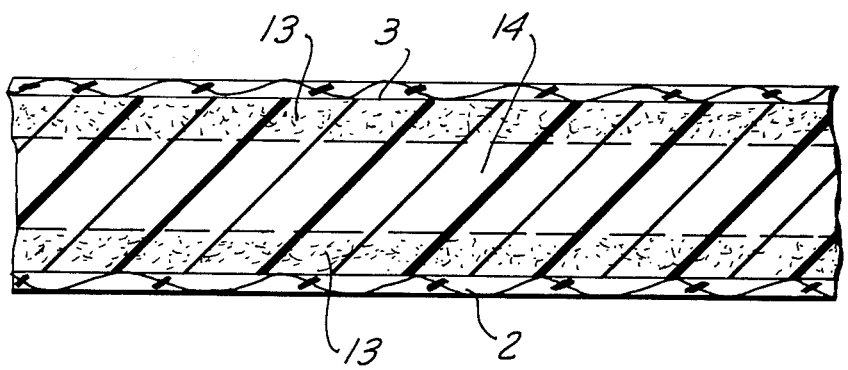
FIG. 3 is a section taken along line III — III of FIG. 2.

From FIG. 3 it will be apparent that the structure of the hard foam mass comprises layers 13 adjacent the elastic fabric hose walls of low-density hard-foam resin while between these layers there is a core 14 of high-density more rigid and less compressible synthetic resin. This core can also be of foam and simply may be more dense because it has less room to expand. The low-density foam 13 provides the desired cushion effect.

In the embodiment of FIG. 4, only the cells 6, 7, 9 of the double sleeve 1 are filled with the hard-foam synthetic resin while the lower cell 8 remains empty. This embodiment is especially suitable for use as a splint.

Of course, instead of inserting the body appendage in the empty interior of the sleeve, the sleeve can be collapsed to form a trough around the body appendage which is held in place by wrapping a bandage around the appendage and the collapsed tube. In the latter case a double wall tubing need not be employed and the reaction mixture can be contained in a simple tube or bag. The embodiment of FIG. 4 permits, as do the embodiments of FIGS. 1 through 3, automatic conformity to the body appendage even when the device is used as a splint.

Figure 5:
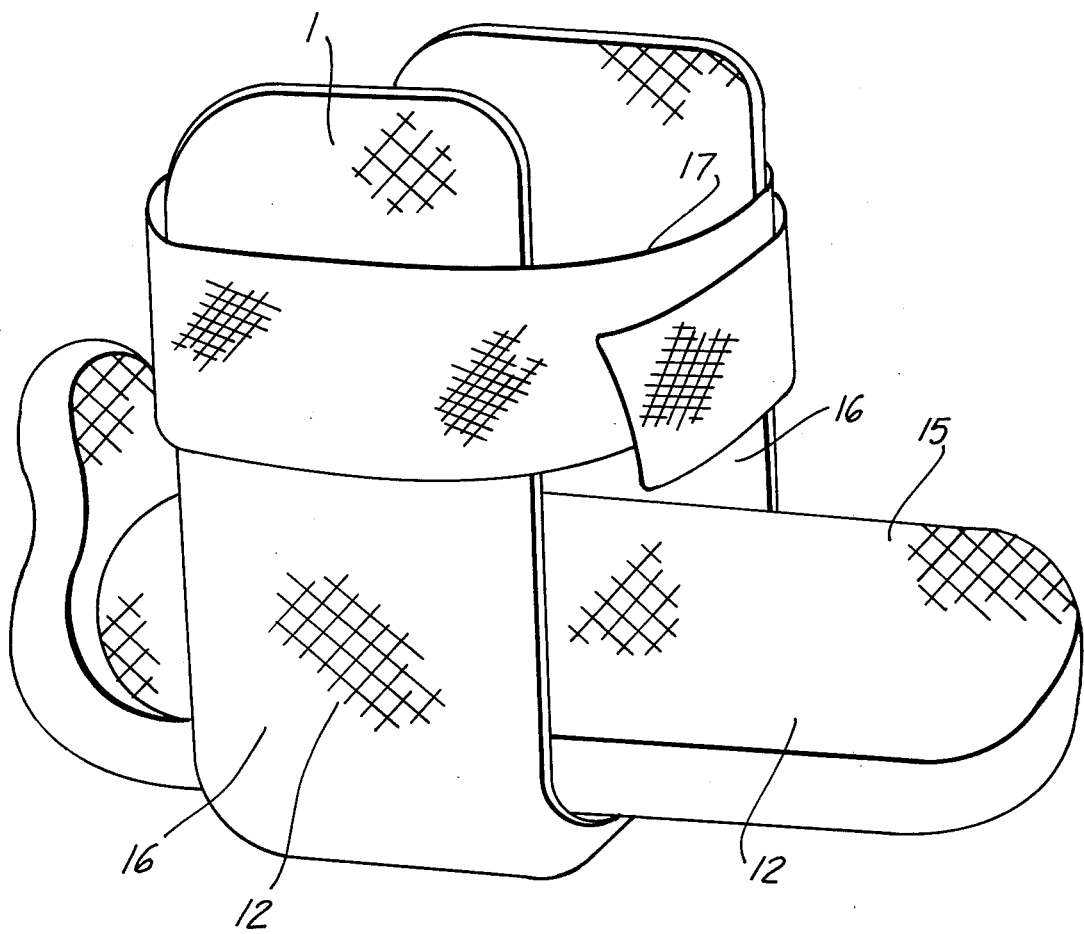
FIG. 5 is a diagrammatical perspective view of the device of the invention for use as a foot splint, brace or supporting structure.

FIG. 5 shows a further embodiment of the invention as well as a totally new technique for applying a support structure to the body using the device according to the invention. For immobilizing and/or supporting the lower leg, ankle or like body portion, a sole plate 15 is provided from a collapsed tube as described in connection with FIGS. 1 through 4. In this case, the reaction mixture is formed within the tubing and the sole of the foot is pressed downwardly thereon except for a rear portion which is bent upwardly over the Achilles tendon. A second collapsed tubing, containing the reaction mixture, is formed as a stirrup with its bight below the sole plate and its legs 16 extending upwardly to flank the lower leg in the ankle region. The shanks 16 are held in place by a bandage 17. When the stirrup 72 and the sole plate 15 set, an effective ankle brace is formed, the ankle brace fully conforming to the leg and being removable by opening the bandage 17.

The hardening time can be adjusted preferably in a range of 5 to 30 minutes so that sufficient time is available to permit exact conformity to the body part to which the device is applied. Furthermore, the hardening time is selected so that there are no unnecessary delays in immobilizing or supporting the body portion.

The invention is of course not confined to the described embodiments but can be used generally in therapeutics, medicine and orthopedics wherever a portion of a human or animal body must be immobilized or supported, whether the body position is an extremity, a portion of the torso, the back or the like.

SPECIFIC EXAMPLE

A tubing having the configuration of FIG. 1 and formed from two elastic cotton stockings joined by spaced-apart webs 5, is closed at the ends of the tube by stitching, and filled with microcapsules consisting of two reactive components, namely, a component A and a component B.

Component A is of the following composition:

Ricinoleyl alcohol: 35 parts by weight
Whiting: 100 parts by weight
Tributylphosphorate: 30 parts by weight
Colloidal silica: 10 parts by weight.

The capsules are formed by rolling a paste of component A into balls and coating them with an alkyd of the type marketed under the name PARAPLEX G-20 by ROHM & HAAS Company. The alkyd is 100% unmodified and has an acid number of 10 to 20, weighing between 0.97 and 9.1 Kg per liter. Although the alkyd remains tacky it is found to be a coherent barrier.

Component B consists of 100 parts by weight of a urethane polymer, e.g., SOLITHIN 113 of THIOKOL Chemical Company having isocyanate reactive terminals, 50 parts by weight whiting, 15 parts by weight colloidal silica and 20 parts by weight of chlorinated biphenyl plasticizer. Blowing agents activated at a temperature of about 40° C may be present in the prepolymer in an amount up to 15 parts by weight (e.g., freon type fluorochlorohydrocarbon).

The coating for the component B is a piccopale resin.

The capsules have diameters of about 5 mm and are filled into the space between the walls of the tubing. For activation, a roller is run over the sleeve and the capsules are crushed, the sleeve being kneaded to insure thorough mixing of the components. The sleeve is then drawn over the body appendage and setting occurs within 30 minutes. The reactive components A and B are provided in 1:1 relationship by weight.

We claim:
1. A device for the immobilization or support of a body part of a human or animal subject comprising a flexible envelope of double-wall tubing having a pair of fabric walls defining an annular space between them, partitions subdividing said space into compartments spaced around the tubing, two interreactive reaction compounds in each of said compartments, and destructi- ble means holding said reaction compounds apart but adapted to be destroyed by an applied effect to permit mixing of said reaction compounds and setting of the resulting reaction mixture to retain a contour applied to said envelope.

2. The device defined in claim 1 wherein said compounds are disposed in respective recesses formed in a foil to which a cover is applied.

3. The device defined in claim 1 wherein said destructible means include layers formed directly on said compounds.

4. The device defined in claim 3 wherein said reaction compounds are provided as microcapsules provided with said layers.

5. The device defined in claim 1 wherein said compounds are received in bags tearable by tension.

6. The device defined in claim 1 wherein said walls are composed of an elastic material.

7. The device defined in claim 6 wherein said partitions are ribs spanning the elastic walls, at least some of said ribs being permeable to connect said compartments.

8. The device defined in claim 7 wherein the inner one of said walls has an elasticity dimensioned such that the inner wall conforms automatically to the body part to be immobilized or supported.

9. The device defined in claim 8 wherein the outer wall has an elasticity dimensioned to impart to the reaction mixture the form of the body part to be immobilized or supported until the reaction mixture hardens.

10. The device defined in claim 7 wherein said walls are composed of fabric having a given residual moisture content.

11. The device defined in claim 7 wherein said ribs are composed of elastic material.

12. The device defined in claim 7 wherein at least some of said ribs are composed of impermeable material capable of forming joints.

13. The device defined in claim 7 wherein at least one of said compartments is free of said compounds and remains free for use of the device as a splint.

14. The device defined in claim 7 wherein said walls are longitudinally and transversely elastic.

15. The device defined in claim 1 further comprising closure means engageable with said envelope for retaining same on said body part.

* * * * *